United States Patent [19]

Gattinoni

[11] Patent Number: 4,844,085

[45] Date of Patent: Jul. 4, 1989

[54] PULMONARY PRESSURE AND VOLUME MEASUREMENT

[76] Inventor: Luciano Gattinoni, Via Porpora 187, Milan, Italy

[21] Appl. No.: 274,696

[22] Filed: Nov. 14, 1988

Related U.S. Application Data

[63] Continuation of Ser. No. 904,139, Sep. 4, 1986, abandoned.

[30] Foreign Application Priority Data

Sep. 13, 1985 [IT]  Italy .................................. 22129/85

[51] Int. Cl.$^4$ .............................................. A61B 5/08
[52] U.S. Cl. .................................................. 128/720
[58] Field of Search ......................... 127/716, 720, 725

[56] References Cited

U.S. PATENT DOCUMENTS

| 348,006 | 11/1969 | Schomber | 128/720 |
|---|---|---|---|
| 3,713,436 | 1/1973 | Hardway, Jr. | 128/720 |
| 4,031,885 | 6/1977 | Davis et al. | 128/720 |
| 4,351,344 | 9/1982 | Stenzler | 128/720 |

FOREIGN PATENT DOCUMENTS

| 2035982 | 1/1972 | Fed. Rep. of Germany . |
| 2077444A | 12/1981 | United Kingdom . |
| 82/01654 | 5/1982 | World Int. Prop. O. . |

OTHER PUBLICATIONS

Measurement and Calculation of Pulmonary Physiological Parameters, U. E. Hedstrand and J. Modig, Med. Progr. Technol, 3, 25-32 (1974).
Derrett et al., "Versatile Micromagnetic . . . Testing", Med. & Biol. Eng. & Comput, 1979, 17, 783-785.
Finucane et al, "Estimation of Alveolarpressure . . . ", J. Appl. Phys., vol. 38, No. 3, Mar. 1975, 531-537.
Cullen, S. C., Anesthesiology, 20:700 (1959).
Mankikian et al., Critical Care Med., 11, No. 11 (1983), p. 897.

*Primary Examiner*—Lee S. Cohen
*Attorney, Agent, or Firm*—Jon S. Saxe; Bernard S. Leon; A. Kate Huffman

[57]  ABSTRACT

A method and a device for measuring mechanical property parameters of the pulmonary system of a patient which comprises;
inflating and deflating the lung with a predetermined gas volume with a pump;
measuring the pressure changes generated in the lung during inflation and deflation with a pressure sensor;
transforming the volume and the measured pressure data into digital form;
calculating typical or clinically significant volume to pressure ratios in a data processor and;
displaying the result of the calculation.

8 Claims, 2 Drawing Sheets

PULMONARY PRESSURE AND VOLUME MEASUREMENT

This application is a continuation of application Ser. No. 904,139 filed Sept. 4, 1986, now abandoned.

BACKGROUND OF THE INVENTION

1. Field of the Invention

The present invention is related with the measurement of mechanical properties of the pulmonary system of a patient and more particularly with the determination of various clinically significant compliance and related parameters of the lung-chest system.

The study of lung mechanics implies the determination of the elastic properties of the lung-chest system. The elastic properties are quantified by successive inflation and deflation of the patient's lungs thereby inducing predetermined air or gas volume changes while simultaneously measuring the corresponding pressure changes.

From the volume/pressure (V/P) relationship, the following parameters (=typical or clinically significant volume to pressure ratios) can be derived:

(a) Total compliance (V/p), wherein V is the inflation volume, of usually 10-15 ml per kg patient weight.

(b) Starting compliance, i.e. the slope of the V/P-curve in its initial portion.

(c) Inflation compliance, i.e. the slope of the V/P curve in its second steeper portion during inflation.

(d) Inflection point or opening pressure, i.e. the knee of the V/P curve between the initial and the steeper portion.

(e) Deflation compliance, i.e. the slope of the V/P curve during deflation.

(f) Unrecovered or "trapped" volume, i.e. the volume in the pulmonary system at the end of deflation, at zero pressure.

(g) Hysteresis area, i.e. the area surrounded by the V/P-curve during inflation and deflation.

(h) Hysteresis ratio, i.e. the hysteresis area divided by the area $V_{max} \cdot P_{max}$.

(i) Best PEEP pressure, i.e. the pressure at which the inflation compliance portion of the V/P curve becomes essentially linear.

2. Background Art

The pressure-volume curve in paralysed patients is presently obtained in two ways: Firstly, by manual inflation and deflation by means of a so-called super-syringe with simultaneous reading of pressures in respiratory ways or, secondly by feeding a constant air or gas flow from a compressed-gas flow generator and independent measurements of resulting pressures.

For obtaining the above-mentioned parameters (a) to (i), complex calculations are required, to be performed separately, which require a long time. Furthermore, the results were not precise enough to be really clinically significant.

SUMMARY OF THE INVENTION

It is an object of the present invention to provide a method and a device for measuring the elastic properties parameters in an accurate and immediate way.

As regards accuracy it has been found that the changes of $CO_2$ and $O_2$ content and the gas temperature measurement significantly influence the V/P curve. It is, thus, another object of the invention to provide a novel system for the accurate measurement of the changes in pressure and volume occurring in the lungs of a patient, wherein during the measurements a compensation is carried out to the purpose of making due allowance for:

(a) the change in volume due to the increase in temperature of air fed to the lungs;

(b) the generation of $CO_2$ in the lungs;

(c) the consumption of $O_2$ in the lungs during the measurement.

A further object of the invention is a biomedical device composed by a mechanical part and an electronic part to carry out the said measurements, which allows not only the measured values to be obtained with greater precision as compared to the known systems, but also the easy and simple setting up and the immediate, displayed obtainment of the measured values.

Further objects and advantages of the invention will become apparent from the following description taken in conjunction with the accompanying drawings of a preferred embodiment of the invention.

DESCRIPTION OF THE DRAWINGS

The preferred embodiment of the invention will now be described with reference to the following drawings, which are merely exemplary and are not meant to limit the scope of the invention in any respects.

FIG. 3 a block diagram of an electronic control and evaluation circuit according to the invention

DESCRIPTION OF THE PREFERRED EMBODIMENT

Figure 1:
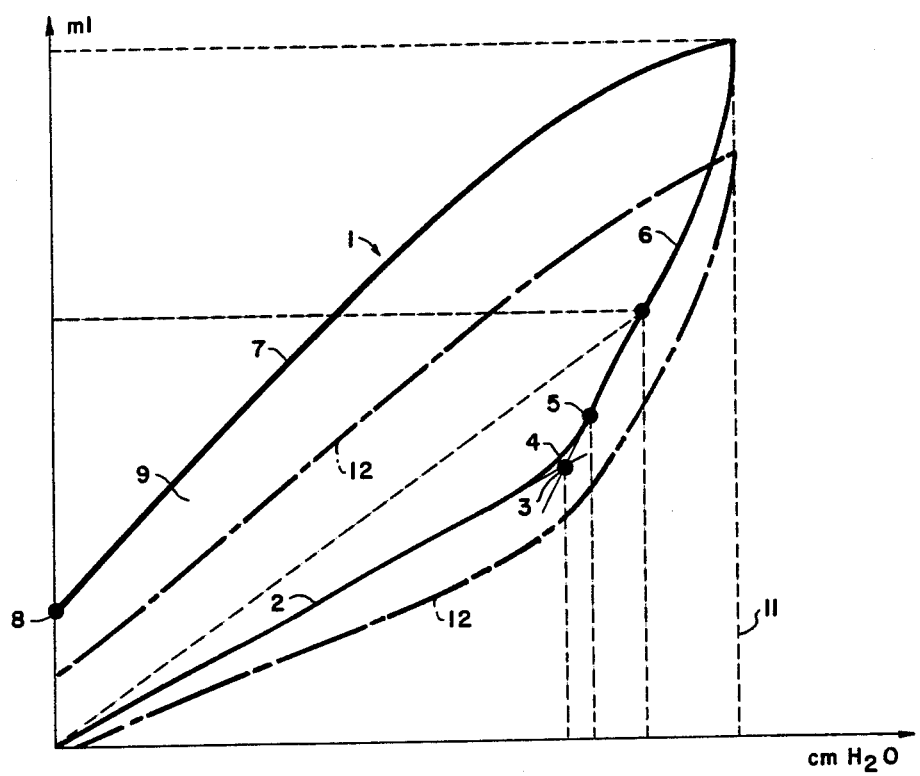
FIG. 1 a typical V/P curve with various significant parameters indicated.

FIG. 1 shows a typical V/P curve 1 obtained by feeding a predetermined volume of e.g. 10 ml per kg patient weight, i.e. about 750 ml for a patient of 75 kg, to a patient with partly intact alveolae and partly injured, collapsed or obstructed alveolae. Usually part of the collapsed alveolae are reopened or recruited upon reaching a certain pressure. The first portion 2 of the curve with a relatively flat slope represents the so-called starting compliance where essentially only the healthy tissue of the intact alveolae is involved.

When the volume fed to the patient has generated a certain pressure, the so-called opening pressure alveolae which were collapsed start to reopen and participate in being ventilated. This point 3 is called inflection point. From there on the curve becomes continuously steeper (shown at 4), i.e. due to the higher lung capacity a higher volume has to be displaced in order to obtain the same pressure difference. When all those alveolae are reopened which can possibly be recruited the curve becomes more or less linear again. The point 5 where this is happening is called best PEEP pressure.

The subsequent essentially linear portion 6 of the curve defines the so-called inflation compliance. After the maximum volume of air has been fed into the patient, deflation starts. The slope of the deflation portion 7 of the curve defines the deflation compliance. The deflation curve ends at a point 8 above zero on the volume axis. This means that at zero pressure not the entire volume fed to the patient has been recovered. The unrecovered or trapped volume is another important parameter in evaluating the lung condition.

Due to the fact that the deflation curve is different from the inflation curve a certain area 9 is surrounded which is called hysteresis. The hysteresis is also considered to be a clinically significant quantity. Finally the hysteresis area 9 can be put in relation to the area $V_{max} \cdot P_{max}$ shown in phantom lines 11. The hysteresis area divided by the area $V_{max} \cdot P_{max}$ is called hysteresis ratio.

Aside from the measured V/P curve 1, FIG. 1 shows a compensated V/P curve 12. The compensated V/P curve will be explained later.

Figure 2:
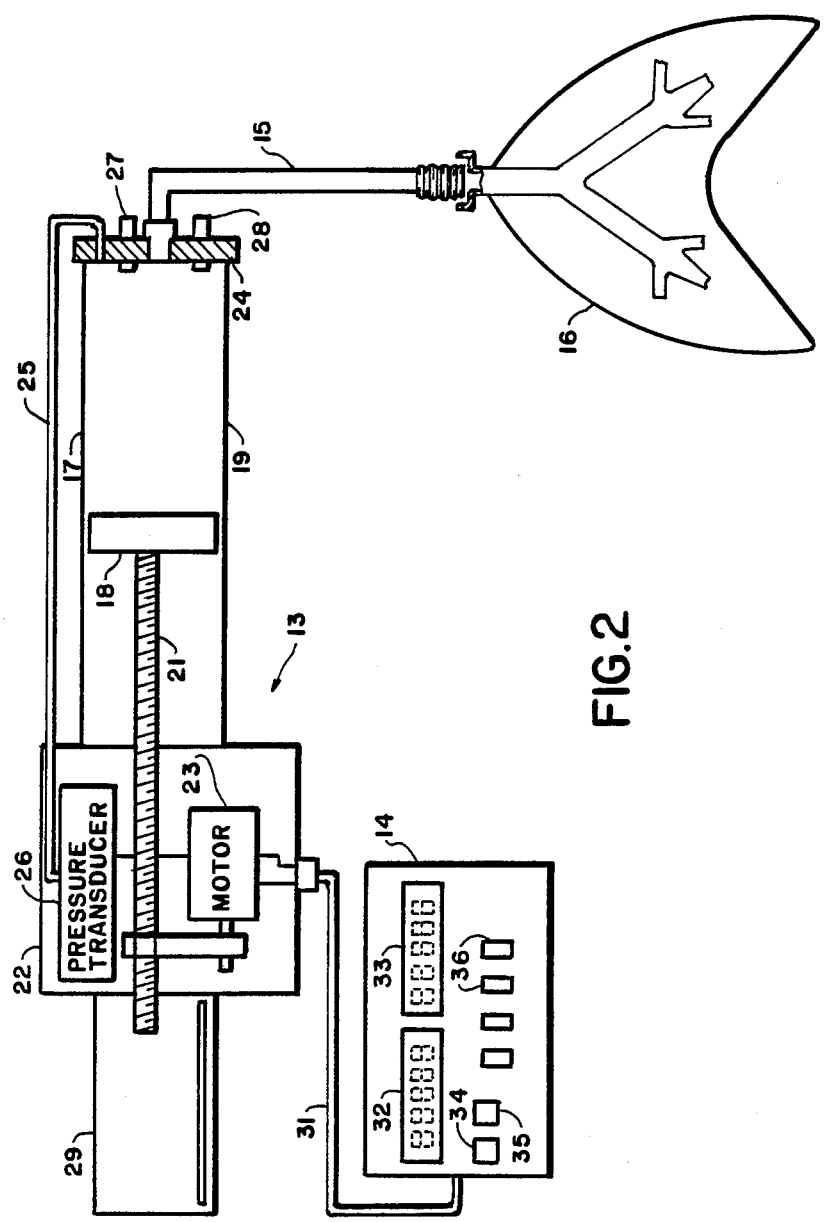
FIG. 2 a schematic view of the mechanical set-up of a preferred embodiment of the invention.

FIG. 2 shows a schematic view of the mechanical configuration of a device for measuring the aforementioned curve and calculating the various significant parameters. The device consists of a pump 13 and an electronic control and evaluation module 14. The pump is connected via conventional tubing 15 to a patient 16 represented by his symbolyzed lung outline.

The pump is constituted by a cylinder 17 preferably made of acrylic glass, in which a piston 18 is provided for reciprocating sliding movement. Depending on the direction of piston movement of air contained in volume 19 is fed via tubing 15 to or withdrawn from the patient 16.

Piston 18 is driven by a conventional worm drive which is represented by threaded rod 21 which is driven by a suitable gear such as a pinion or belt drive (not shown) inside casing 22. The gear is driven by a step motor 23. Cylinder 17 is mounted on casing 22 by means of a head plate 24 which is held by screw bolts or rods (not shown) to press cylinder 17 against casing 22 to assure air-tight conditions. This kind of mounting assures at the same time quick and easy disassembling for sterilization purpose. The head plate 24 is provided with a socket for connection with tubing 24 and with a further socket for connection with a tube 25 leading to a pressure transducer 26 inside casing 22. Head plate 24 further carries an unidirectional delivery safety valve 27 which is calibrated for a maximum pressure of 0.75-0.8 bar and an unidirectional filling return safety valve 28 calibrated for a maximum pressure of 0.05 bar.

Casing 22 is preferably made of aluminum and is provided with one or more handgrips (not shown) for handling and transportation. On the side opposite to cylinder 17 the casing 22 has a projecting housing portion 29 for covering the threaded rod 21.

An electrical connection cable 31 leads from the casing 22, inside which it is connected to motor 23 and pressure transducer 26 to module 14. Module 14 contains the electronic control and evaluation circuitry to be described in connection with FIG. 3. In FIG. 2 the front panel of module 14 is shown to contain two digital displays 32 and 33, a red LED indicating light 34 and a grean LED indicating light 35 for informing on the selected operation mode. Moreover the front panel is equipped with a number of push button switches 36 to feed the necessary commands into the circuit.

FIG. 3 shows a block diagram of the control and evaluation circuitry contained in module 14. The central component is a microprocessor 37 containing a 4 MHz clock. In the present embodiment a type Z80 manufactured by Zilog is used. Connected to microprocessor 37 are a read only memory 38 and a random access memory 39. Memory 38 contains the program used by processor 37 for control of motor 23 and for measuring and computing measured values. Memory 38 has a capacity of 16 kbytes. Memory 39 is used to store input data, measurement results and computation results to be displayed of recorded. It has a capacity of 2 kbytes.

Pressure data signals from pressure transducer 26 are 0 to 5 volt analog signals which are fed via a conventional filter 41 equipped with operation amplifiers and from there via a conventional analog/digital converter 42 to microprocessor 37.

Processor 37 upon command from the program stored in memory 38 produces motor activating signals to cause motor power supply 43 to feed electrical driving signals to motor 23 thus generating step-wise or continuous motion of piston 18 in cylinder 17.

The output data generated by processor 37 are fed to a display driver/multiplexer 44 and from there reach one of the digital displays 32,33 or of the indicator lights 34,35.

Input data such as choice of operation mode, volume, cycle time etc. are fed to processor 37 via push buttons or keys 36, and are usually stored in memory 39.

Some of the push buttons or keys shown on the front panel of module 14 may as well be associated with the pump unit. This is true particularly for the start button for the motor.

The power supply is not particularly shown because it consists of conventional transformers, rectifiers, filters and voltage regulators as well as fuses for safety purposes.

When in operation the processor 37 following the program stored in memory 38 generates and sends a certain number of step-controlling pulses to motor 23. As each step corresponds to an angular displacement of the motor axis of 1.8°, in accordance with the construction data of the piston and cylinder configuration a volume of 0.1178 ml is displaced. Hence the volume is clearly defined by the number of steps. It is not necessary to measure the volume by a flow meter.

The pressure in cylinder 17 is sensed by pressure transducer 26 and the pressure signal is fed to processor 37. Accordingly processor 37 continuously has the volume and pressure data and calculates the various characteristic parameters of the volume/pressure curve. The results of the calculations are stored in memory 39 and displayed upon demand.

As already mentioned it has been found by the inventor that the volume/pressure relationship is influenced by certain effects such that the measured data are incorrect. Due to a temperature increase of the air fed to the patient from ambient temperature to 37° C. the volume actually given to the patient is higher than that produced by the piston displacement. Another effect is the oxygen consumption in the lung which is only partially compensated by the carbon dioxide generation in the lung. Still another effect is caused by the volume change due to gas pressurising and depressurizing. These effects apparently compensate each other in part but compensation is different during inflation and deflation. While the volume change caused by temperature change during inflation is at least partially made up for during deflation, the volume loss due to oxygen conssumption is not. Further, certain of the volume changes depend on the cycle time, i.e. the longer the air is in the lungs the more oxygen is lost.

It has further been found by the inventor that these inaccuracies cause substantial variations in the computed parameters so that the clinical signifance of these parameters becomes doubtful. In order to improve the accuracy a compensation or correction is effected during processing of the measured values. The corrected V/P curve 12 is shown in phantom line in FIG. 1.

The correction for the volume changes due to the temperature difference between ambient and lung temperatures, the $CO_2$ generation and the $O_2$ consumption is made by processor 37 according to the following formula $$V_{eff} = V_{step} \pm 0{,}116 V_{step} - V_{comp} \cdot (T/60)$$

wherein $V_{eff}$ is the corrected or compensated volume, $V_{step}$ is the volume displaced by piston 18 based on the cylinder and piston geometry, the factor 0,116 is an experimental factor found to be an optimum by the inventor, $V_{comp}$ is a volume which compensates for the net oxygen loss ($CO_2$ generation taken in consideration), T is cycle time in seconds. The sign + or − in case of the first compensation volume take care of inflation (+) and deflation (−).

The various features and advantages of the invention are thought to be clear from the foregoing description. Various other features and advantages not specifically enumerated will undoubtedly occur to those versed in the art as likewise will many variations and modifications of the preferred embodiment illustrated, all of which may be achieved without departing from the spirit and scope of the invention as defined by the following claims.

I claim:

1. Device for determining static mechanical properties of a paralyzed patient's lung comprising
    pump means communicating with a paralyzed patient's lung to feed to and withdraw from the patient's lung a predetermined gas volume;
    pressure sensor means connected to said pump means for sensing the gas pressure in the lung;
    data processing means for processing the volume and pressure data to result in a continuous generation of volume pressure ratio data for determining static mechanical properties of the paralyzed patient's lung; and
    control means for controlling the pump means.

2. Device according to claim 1, wherein the pump means contains a motor-driven piston pump which is adapted to be connected to the patient's lung.

3. Device according to claim 1, wherein the data processing means contain a microprocessor and memory means for permanent storage of program data and for preliminary storage of input and output data.

4. Device according to claim 3 wherein the data processing means moreover contain display and indicating means.

5. A method of determining the mechanical properties of a lung of a paralyzed patient comprising
    feeding a predetermined gas volume into the lung thereby inflating the lung and thereafter releasing the gas volume, thereby deflating the lung
    measuring the pressure changes generated in the lung during inflation and deflation so as to obtain data
    transforming the volume and the measured pressure data into digital form
    calculating typical or clinically significant volume to pressure ratios, and
    displaying the result of the calculation.

6. Method according to claim 5 wherein the inflating and deflating is effected stepwise with incremental volume changes.

7. A method of determining the mechanical properties of a paralyzed patient's lung using a pump means having a piston within a cylinder with a predetermined displacement, comprising
    feeding a predetermined gas volume into the lung thereby inflating the lung and thereafter releasing the gas volume, thereby deflating the lung
    measuring the pressure changes generated in the lung during inflation and deflation so as to obtain data
    correcting a volume data according to a formula $$V_{eff} = V_{step} \pm 0.116 V_{step} - V_{comp} \cdot (T/60)$$

wherein $V_{eff}$ is the corrected or compensated volume, $V_{step}$ is the volume displaced by the piston based on the cylinder and piston geometry, $V_{comp}$ is a volume which compensates for the net oxygen loss ($CO_2$ generation taken in consideration), T is cycle time in seconds
    calculating typical or clinically significant volume to pressure ratios, and
    displaying the result of the calculation.

8. Method according to claim 7 wherein the inflating and deflating is effected stepwise with incremental volume changes.

* * * * *